United States Patent [19]

Meyer

[11] Patent Number: 5,027,792
[45] Date of Patent: Jul. 2, 1991

[54] ENDOSCOPIC REVISION HIP SURGERY DEVICE

[75] Inventor: William F. Meyer, Walnut, Calif.

[73] Assignee: Percutaneous Technologies, Inc., Walnut, Calif.

[21] Appl. No.: 452,970

[22] Filed: Dec. 19, 1989

Related U.S. Application Data

[63] Continuation-in-part of Ser. No. 325,652, Mar. 17, 1989, abandoned.

[51] Int. Cl.$^5$ ............................................. A61B 1/00
[52] U.S. Cl. ........................................ 128/6; 604/22; 606/46
[58] Field of Search ............... 128/4, 6, 7; 604/21, 604/22, 27, 43; 606/28, 46, 49, 19; 600/9

[56] References Cited

U.S. PATENT DOCUMENTS

| | | | |
|---|---|---|---|
| 1,952,617 | 3/1934 | Wappler | 606/46 |
| 2,038,393 | 4/1936 | Wappler | 128/7 |
| 2,583,937 | 1/1952 | Fossati | 128/4 |
| 2,888,928 | 6/1959 | Sieger | 606/49 |
| 3,294,085 | 12/1966 | Wallace | 128/6 |
| 3,528,424 | 9/1970 | Ayres | 606/19 |
| 3,618,611 | 11/1971 | Urban | 128/305 |
| 3,782,373 | 1/1974 | Smythe | 128/92 |
| 3,791,379 | 2/1974 | Storz | 128/4 |
| 3,850,175 | 11/1974 | Iglesias | 128/7 X |
| 3,900,022 | 8/1975 | Widran | 128/7 |
| 3,906,955 | 9/1975 | Roberts | 604/21 X |
| 3,974,833 | 8/1976 | Durden, III | 606/49 X |
| 4,132,227 | 1/1979 | Ibe | 128/4 |
| 4,203,444 | 5/1980 | Bonnell et al. | 128/276 |
| 4,550,716 | 11/1985 | Kinoshita | 128/6 |
| 4,562,838 | 1/1986 | Walker | 606/49 X |
| 4,587,957 | 5/1986 | Castel | 600/9 |
| 4,598,710 | 7/1986 | Kleinberg et al. | 128/751 X |
| 4,601,284 | 7/1986 | Arakawa et al. | 128/6 |
| 4,607,621 | 8/1986 | Wheeler | 128/6 |
| 4,681,561 | 7/1987 | Hood et al. | 604/22 |
| 4,719,914 | 1/1988 | Johnson | 606/28 |
| 4,750,902 | 6/1988 | Wuchinich et al. | 604/43 X |
| 4,756,309 | 7/1988 | Sachse et al. | 128/6 X |
| 4,844,062 | 7/1989 | Wells | 128/6 X |
| 4,865,018 | 9/1989 | Kanno et al. | 128/6 |

*Primary Examiner*—William H. Grieb

[57] ABSTRACT

An endoscopic resecting system views and resects a grouting agent or osseus tissue from the femoral canal during revision hip surgery. The endoscopic system includes a compartmentalized tube, a visualizing device, an illuminating device, a first resecting mechanism, an irrigating apparatus and an aspirating apparatus. The compartmentalized tube has a first compartment of a first set of dimensions and a second compartment of a second set of dimensions larger than the first set of dimensions. A portion of the visualizing device is disposed in the first compartment so it directly views the grouting agent. A portion of the resecting mechanism is disposed in the second compartment. A portion of the irrigating apparatus is disposed in the first compartment. A portion of the aspirating apparatus is disposed on the second compartment so that it removes debris created during the process of resection. The visualizing device, the illuminating device, the first resecting mechanism, the irrigating apparatus and the aspirating apparatus are all contained within the same structure in order to function in an integrated and coordinated manner.

12 Claims, 4 Drawing Sheets

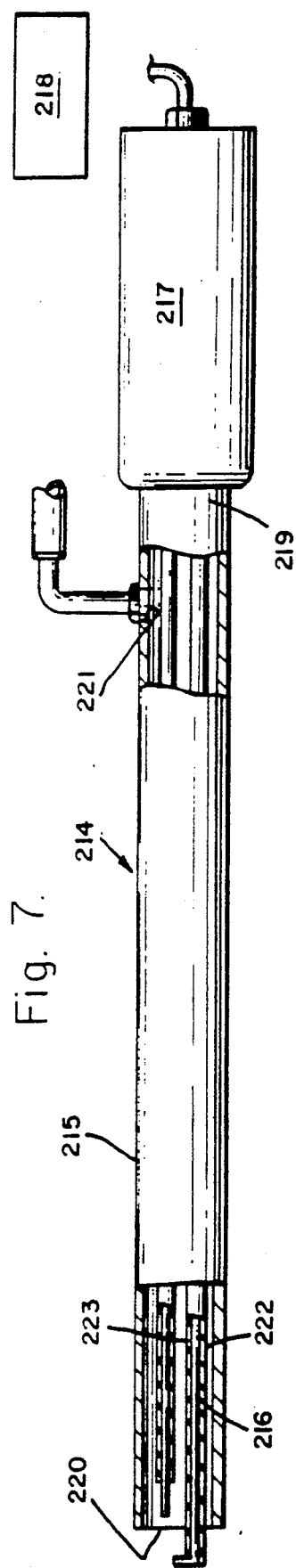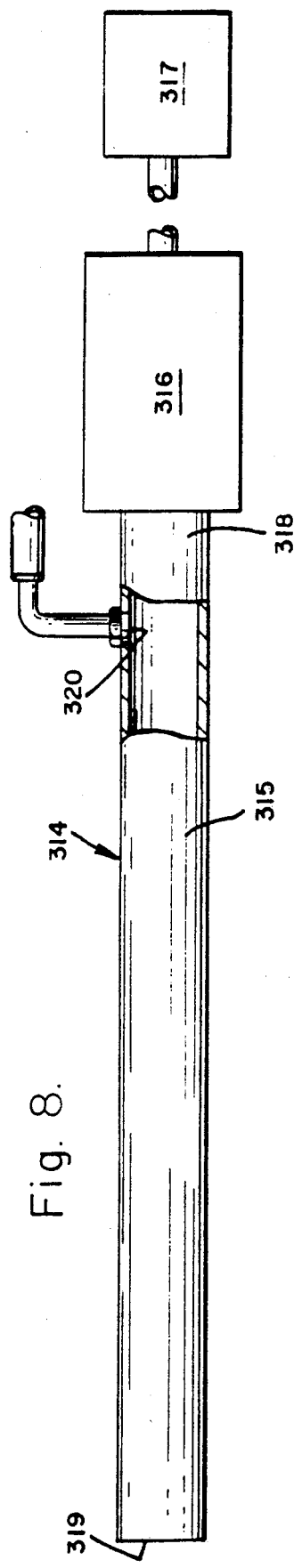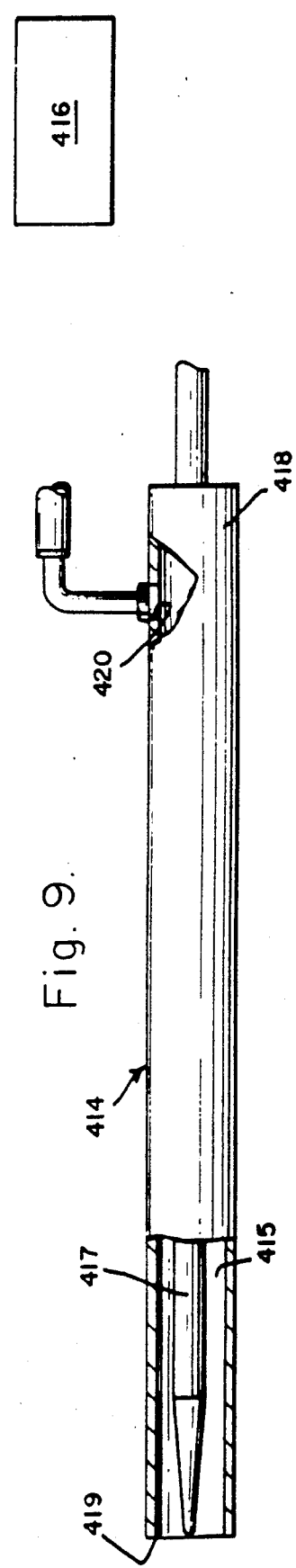

ENDOSCOPIC REVISION HIP SURGERY DEVICE

The application is a continuation-in-part of an application, filed Mar. 17, 1989 under Ser. No. 325,652, now abandoned.

BACKGROUND OF THE INVENTION

1. Field of the Invention

This invention relates to a endoscopic resecting system which removes methyl-methacrylate (bone cement) or some other grouting agent and ossues tissue from the human body femoral canal during revision hip surgery to treat arthritis of the hip joint.

2. Description of Prior Art

Normal method for treatment of severe arthritis of the hip involves performing an internal amputation of the proximal end of the femur, and its replacement with an appropriately shaped metallic device. A spacer or grouting agent, methylmethacrylate, called bone cement, is used to seat and secure the metal implant into the femur. As the patient walks or runs on the implant after the primary procedure, the bone cement, being brittle, begins to crack and as a result the implant loosens, causing the original arthritic pain to return. Eventually, the metallic femoral implant must be replaced. Bone cement, so effective during the initial procedure, now becomes a major problem because it must be meticulously removed, lest it become a nitus for failure of the replacement prosthesis.

Pneumatically operated devices and manual instruments are currently used to remove cement and completely clean out the femoral canal. Pneumatic motors are difficult to operate, require heavy hoses to connect motor to source of gas, can require tanks of air to be placed in a surgical environment that is keep very clean by use of hepa-filters, and vent unsterile air into this same clean environment. In performing a patent search, specific patents which describe this pneumatic motor technology have not been identified. Use of manual instruments is performed cautiously and as a result extends operating time and general anesthesia time. Manual instruments designed for this surgical procedure are not described or claimed in patents currently in force. Other forms of energy are being employed experimentally to accomplish the same.

With an aging population, treatment of hip arthritis by hip replacement will be more common. Likewise, revision of the first implant operation will be more common. Therefore, there is significant need for a device which will make this surgical procedure more effective.

The problem confronting the orthopaedic surgeon performing this procedure is that the surgeon must work at the end of a six to eight inch deep, dark hole in the femur that has an opening about one inch across. Into this hole are introduced high speed, greater than 50,000 rpms pneumatically or hand operated sharp cutting tool which occupy half of the opening. Then the surgeon must look past these impediments to visualize down to the end of this dark hole. As a result, it is difficult to differentiate between cement which must be removed and the underlying cortical bone, which must not be removed.

Given these conditions, sharp tools, necessary to remove cement, are not effectively controlled with the result that undesired holes or perforations are cut in the femur and are common. When perforation occurs, a 6-8 inch extension of the surgical wound, distally down the shaft of the femur is required, along with debridement of the perforation, and usually bone graft to correct the defect. This results in considerably greater pain, suffering, and morbidity, about an hour additional general anesthesia time, and more cost. Sometimes the final condition which results is osteomyelitis, a whole new form of orthopaedic malady, with significantly higher morbidity and complications.

Although a fluoroscopic image intensifier can be used to identify impending perforation out of the shaft of the femur, more likely it will confirm perforation rather than prevent it. Use of a flouroscope dictates exposure to cancer causing x-rays or related use of heavy lead aprons by operating room persons, both of which add to the difficulty of this already difficult procedure.

Related prior art involves small diameter, optical medical telescopes which have been used for orthopaedic arthroscopy for several years, and other surgical procedures for decades. Arthroscopes have a shape and size that make them beneficial in performing the arthroscopic technique, but not effective for performing revision hip surgery.

Additional related prior art is fiber optic light illuminators that are used for medical, endoscopic surgical procedures in general and for orthopaedic arthroscopy in particular. These light sources do not provide the light intensity to properly illuminate the femoral canal, and produce clear images with the medical video camera system that is used in conjunction with the femoral canal endoscope.

Additional related prior art is a peristaltic pump used to instill fluid, usually normal salline, into a body cavity to expand its volume, and provide a clear liquid medium to view the body cavity using a generic type of endoscope. This instilled fluid may be removed from the body cavity either through the endoscope or through a separate outflow conduit, usually by applying active suction to the conduit and conecting PVC tubing, the suction being generated by some aspirating external pump. Precise control of rate of inflow is not achieved with prior art instilling pumps, and coordination of volume of inflow to volume of aspiration, through electronic controls is not characteristic of these forms of prior art.

Related prior art are machines which function independently including light source illuminators, and peristaltic pumps, used for surgical procedures other than indicated in this patent application.

Additional related prior art is a high speed, pneumatically powered motor which drives a sharp burr that actually abrades away the cement. A pneumatic motor requires difficult to use compressed air tanks. Prior art devices vent unsterile air into an environment that is attempted to be kept meticulously clean by circulation of this air through hepafilters.

U.S. Pat. No. 4,132,227, entitled Urological Endoscope Particularly Resectoscope, issued to Wolfgang Ibe on Jan. 2, 1979, teaches a hollow cylinder sheath, a viewing device, an illuminating device, a resecting device and an outflow tube The hollow cylinder sheath has a proximal end and a distal end. The viewing device is an endoscopic arrangement of optical elements. The illuminating device is a cooperating arrangement of fiber optics which is optically coupled to a light source. The viewing device and the illuminating device are located in the sheath extending from the distal end back to the proximal end. The outflow tube is slidable onto the sheath to surround the sheath and form together with the sheath an intermediate return-flow space between the outer wall of the sheath and the inner wall of the outflow tube, with the outflow tube when in position slid over the sheath tightly surrounding the distal end portion of the sheath. The resecting device is an electrode loop which is electrically coupled to an electromagnetic energy source. Clear rinsing water is introduced into the proximal end of the sheath. Turbid water is removed from the proximal end of the intermediate space. The outflow tube is provided with apertures at the distal end thereof for the flow of clear rinsing water out of the distal end of the sheath and around the end of the endoscope and then through the apertures into the intermediate space. U.S. Pat. No. 4,607,621, entitled Endoscopic Apparatus, issued to Robert C. Wheeler on Aug. 26, 1986, teaches an insertion tube, an electrosurgical generator and an electrode loop which is electrically coupled to the electrosurgical generator.

U S. Pat. No. 4,756,309, entitled Endoscope for Removal of Tissue, issued to Hans-Ernst Sachse on July 12, 1988, teaches an endoscope which resects tissue inside body cavities and which includes a hollow outer tube, a rotating shaft and a flushing duct. The shaft carries a grinding or milling head which allows precise removal of scar tissue or other fairly firm tissue under endoscopic control without leaving irregular or thermally damaged wound sites. The endoscope also includes a tube for a lens system and cold light guide and an eyepiece.

U.S. Pat. No. 4,844,062, entitled Rotating Fiberoptic Laser Catheter Assembly with Eccentric Lumen, issued to Lisa D. Wells on July 4, 1989, teaches a catheter assembly which includes a catheter and an optical fiber. The catheter defines a first eccentric lumen which encompasses the center of the catheter and a second lumen. The optical fiber runs through the first eccentric lumen and has a distal end which is eccentric to and encompasses the center of the catheter. U.S. Pat. No. 4,865,018, entitled Control Apparatus for Endoscopes, issued to Masahide Kanno, Katasuyaki Saito and Akihiko Miyazaki on Sept. 12, 1989, teaches a control apparatus which controls a plurality of functions of an endosocpe. U.S. Pat. No. 4,550,716, entitled Liquid Supplying Device for Endoscope, issued to Kunio Kinoshita on Nov. 5, 1985, teaches a liquid supplying device which includes a housing with a connecting portion to which a connector of an endoscope is connected. The liquid supplying device also includes a lamp, an air pump, and a liquid supply tank.

U.S. Pat. No. 3,618,611, entitled Vacuum Rotary Dissector, issued to Julius C. Urban on Nov. 9, 1971, teaches a vacuum rotary dissector which includes a support, an outer tubular member, an inner tubular member and a motor. The outer tubular member extends from the support and has a closed generally hemispherical distal end and a first laterally directed opening adjacent to its distal end extending axially along the outer tubular member and partially along the closed generally hemispherical distal end. The inner tubular member is rotatably mounted in the outer tubular member and has a complementary generally hemisperical distal end frictionally bearing on an inner complementary surface of the closed generally hemispherical distal end of the outer tubular member. The inner tubular member has a second laterally directed opening coextensive with the first laterally directed opening defining generally axially extending cutting edges coincident with the inner surface of the outer tubular member. The motor continuously rotates the inner tubular member relatively to the support and the outer tubular member.

U.S. Pat. No. 4,598,710, entitled Surgical Instrument and Method of Making Same, issued to Larry K. Kleinberg and Donald S. Evans on July 8, 1986, teaches an arthroscopy shaver which includes a pair of co-axially assembled tubes. The tubes have their distal walls in bearing relationship and with registrable openings extending through such distal and annular walls correspondingly joined to their respective distal walls. U.S. Pat. No. 4,203,444, entitled Surgical Instrument Suitable for Closed Surgery Such as of the Knee, issued to Leonard J. Bonnell, Edward H. McHugh, Douglas D. Sjostrom and Lanny L. Johnson on May 20, 1980, also teaches an arthroscopy shaver.

SUMMARY OF THE INVENTION

In view of the foregoing factors and conditions which are characteristic of the prior art it is the primary object of the present invention to provide an endoscopic resecting system which permits the orthopaedic surgeon to view within the femoral canal to observe location of some form of grouting agent or osseus tissue, and remove it differentially from cortical bone by some manual instrument such as an orthopaedic osteotome which is not part of the present invention.

It is another object of the present invention to provide an additional design of endoscopic resecting system which not only permits the orthopaedic surgeon to view within the femoral canal to observe location of a grouting agent or osseus tissue but also incorporates in this component of the system a means to accomodate a resecting device for removing the grouting agent or osseus tissue, with the resecting device placed in the precise position to allow direct visualization of the grouting agent or osseus tissue as it is being resected.

It is still another object of the present invention to provide a means for support of the grouting agent or osseus tissue resecting component, within a compartmentalized tubee, allowing the grouting agent or osseus tissue resecting component to function properly, and protecting the optical component of the medical telescope from damage during this process.

It is yet another object of the present invention to provide a means for instilling fluid into the femoral canal, to move debris away from the end of the endoscope to maintain clear vision, lubricate the grouting agent or osseus tissue resecting component if necessary, and also provide a vehicle for transport of debris created during the resecting process, to the outside of the human body.

It is yet still another object of the present invention to provide efficient, more easily operated energy sources to create and/or deliver into the femoral canal the proper forms of energy that are used to actually perform the cement removal process.

It is yet still another object of the present invention to provide a very high intensity light source as component of the system, which generates appropriate forms and quantity of light sufficient to properly illuminate and/or differentiate structures within the canal for observation, when a small size video camera is attached to the proximal end of the endoscope.

It is still yet another object of the present invention to provide a means for controlled inflow of fluid into and aspiration of fluid from the femoral canal to maintain clear viewing of the femoral canal during the surgical procedure and efficient transport of debris which is created during the resection of the grouting agent or osseus tissue from the femoral canal.

It is still a further object of the present invention to provide an interrelated and coordinated system of energy sources within the same physical chasis including light source, energy source to resect the grouting agent or osseus tissue, and energy source to inflow and control aspiration of a transporting medium, with the chasis modularized for efficient service.

The features of the present invention which are believed to be novel are set forth with particularity in the appended clams.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 7 is a longitudinal view of a third resecting mechanism of a third endoscopic resecting system which includes a console and an endoscopic viewing and resecting apparatus and which has been made in accordance with the principles of the third embodiment of the present invention.

FIG. 8 is a longitudinal view of a fourth resecting mechanism of fourth endoscopic resecting system which includes a console and an endoscopic viewing and resecting apparatus.

DESCRIPTION OF THE PREFERRED EMBODIMENT

Figure 1:
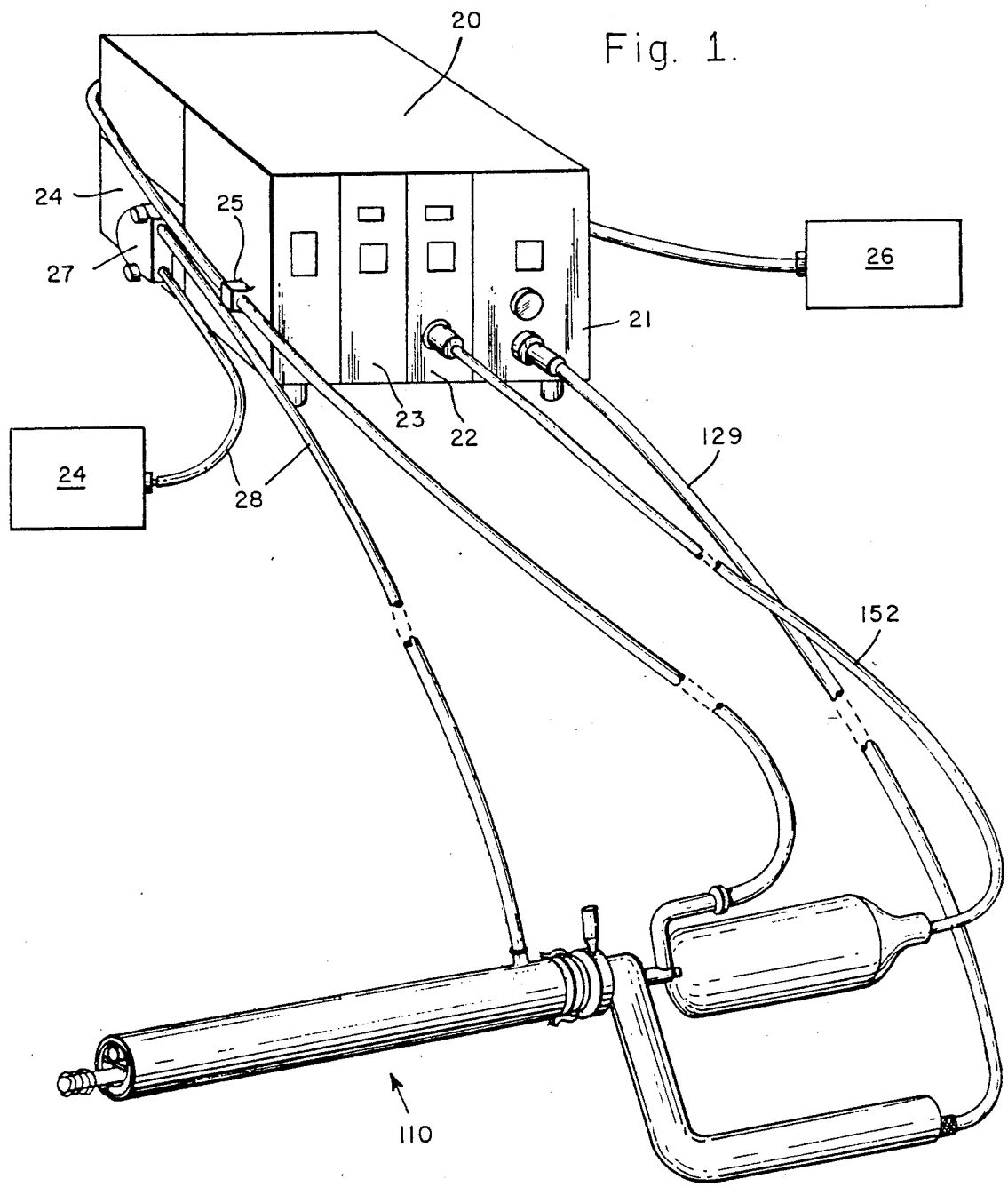
FIG. 1 is a perspective drawing of a first endoscopic resecting system which includes a console and a first endoscopic viewing and resecting apparatus and which has been made in accordance with the principles of the first embodiment of the present inventon.

In order to best understand the present invention it is necessary to refer to the following description of its preferred embodiment in conjunction with the accompanying drawing. Referring to FIG. 1 an endoscopic resecting system 10 includes a console 20 and an endoscopic viewing and resecting apparatus 110 for viewing and resecting a grouting material or an osseus tissue from the femoral canal. The console 20 includes at least four separate modules which are a light source module 21, a motor module 22, a transport medium pump control 23, and transport medium peristaltic pump module 24. On the front side of the light source module 21 are its operating controls which include an on/off toggle power switch, a light source intensity digital read-out, an intensity adjusting rheostat, and a fiber optic cable connection. On the front side of the motor module 22 are its operating controls which include an on/off toggle power switch, a motor speed adjustment, and a motor handpiece connection. The electronic components of the motor module 22 include a connection to a 110 volt external power supply, an on/off toggle power switch, a printed circuit board, a transformer, a heat sink, a speed adjusting control and motor handpiece connection. The console 20, which is electrically coupled to a 110 volt external power supply, also includes an on/off toggle power switch, a power supply, a lamp, a lamp cooling fan, a digital readout of intensity, and a protecting glass and a light intensity measuring device. The non-elecrtonic components of the console 20 also include support brackets for the power supply, the rheostat used to adjust light intensity, the aperture plate, the light attenuator, the fiber optic cable holder and the lourves near the lamp and in line with air flow from the fan.

Still referring to FIG. 1 on the front side of the transport medium pump controls module 23 are its operating controls which include an on/off inflow pump and suction control toggle switch, an inflow rate digital read-out, and inflow rate adjusting rheostat and a suction pressure adjusting rheostat. On the side of the transport medium pumps controls module 23 is a suction tube occluding device 25 which regulates suction pressure from a suctioning apparatus 26. The tube occluding device 25 is adjusted to regulate the outflow of the saline and the resected tissue from the surgical site. The transport medium pump controls module 23 includes a connection to a 110 volt external power supply, an on/off toggle power switch, an inflow rate digital read-out, an inflow rate adjusting rheostat, a printed circuit board for the pump and controls, a printed circuit board for the suction controls, and a suction pressure adjusting rheostat. On the side of the peristaltic pump module 24 is a pump tubing holder 27 which is mechanically coupled to inflow tubing 28. A saline source 29 is fluidly coupled to the inflow tubing 28. The electronic components of the peristaltic pump module 24 include a connection to pump controls module, a transformer and a motor. The non-electronic conmponents of the peristaltic pump module 24 include a system of torque dampeners, a pump driver, the peristalltic action producing wheel and a mechanical connector from motor shaft to peristaltic action producing wheel.

Figure 2:
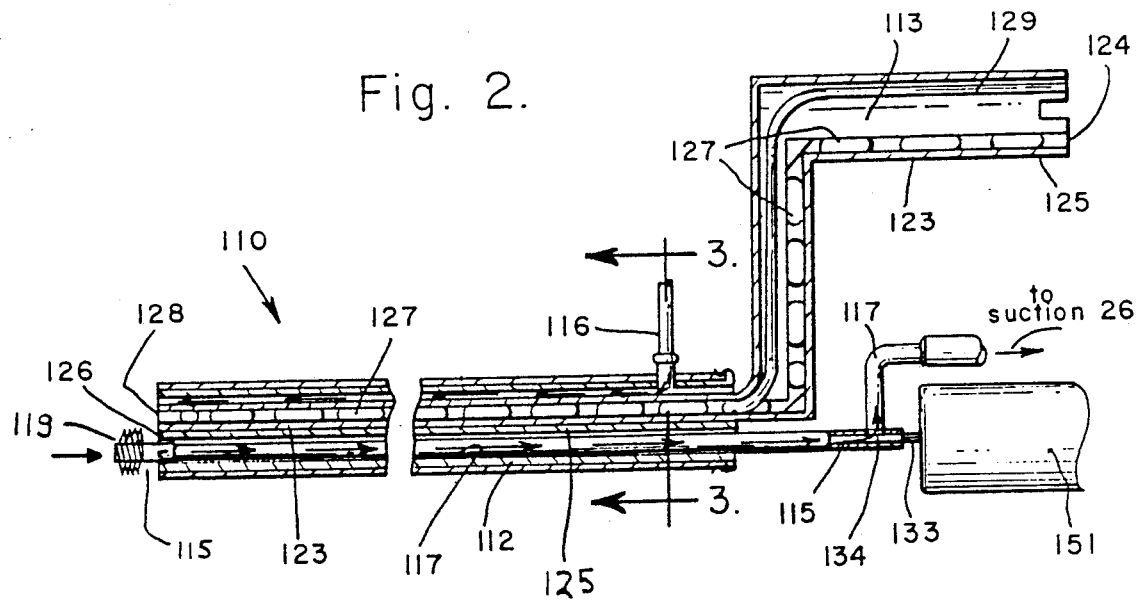
FIG. 2 is a partial longitudinal cross-sectional view of the first endoscopic viewing and resecting apparatus of FIG. 1 which includes a compartmentalized tube, an insulating barrier between the compartments of the tube, a viusualizing device, an illuminating device and a first resecting mechanism.
Figure 3:
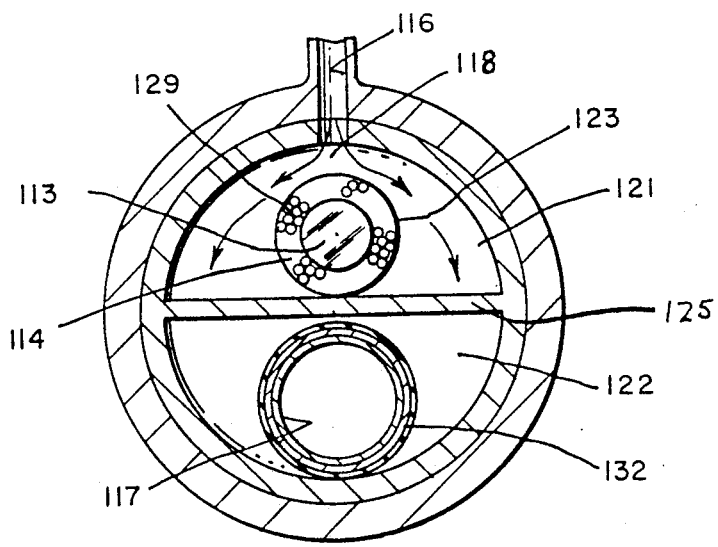
FIG. 3 is a transverse cross-sectional view of the first endoscopic viewing and resecting apparatus of FIG. 1 taken along the line 3—3 of FIG. 2 which also includes a compartmentalized tube, an insulating barrier between the compartments of the tube, an irrigating apparatus and an aspirating outflow apparatus.

Referring to FIG. 2 in conjunction with FIG. 1 and 3 the endoscopic viewing and resecting apparatus 110 includes a compartmentalized tube 112, a visualizing device 113, an illuminating device 114, a first resecting mechanism 115, an irrigating apparatus 116, and an aspirating apparatus 117. The suctioning apparatus 26, which is provided in the operating room, is fluidly coupled to the aspirating apparatus 117. The irrigating apparatus 116 has an inflow connector 118 which is mechanically coupled to the compartmentalized tube near its proximal end and which is fluidly and mechanically coupled to the saline source 29 by the inflow tubing 28.

Figure 4:
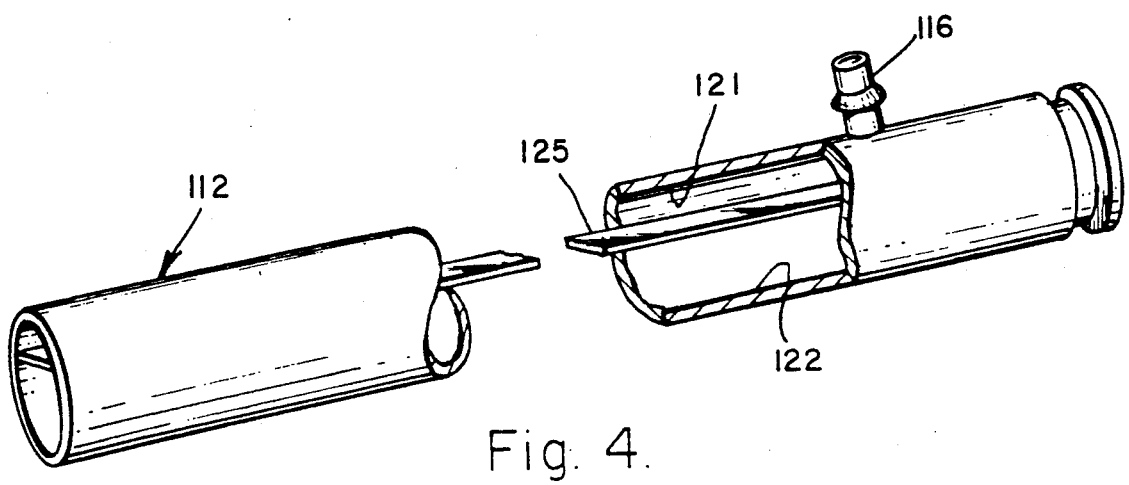
FIG. 4 is a partial perspective drawing of the compartmentalized tube and insulating barrier of the first endoscopic viewing and resecting apparatus of FIG. 1.

Referring to FIG. 4 in conjunction with FIG. 2 and FIG. 3 the compartmentalized tube 112 has a first compartment 121 of a first set of dimensions, a second compartment 122 of a second set of dimensions larger than the first set of dimensions, and a barrier 125 between the first and second compartments constructed from an energy absorbing material. The visualizing device 113 directly views the grouting material or osseus tissue. A portion of the visualizing device 113 is disposed in the first compartment 121. The illuminating device 114 provides illumination of the grouting agent or osseus tissue. A portion of the illuminating device 114 is disposed in the first compartment 121. The first resecting mechanism 115 resects the grouting agent or osseus tissue. A portion of the first resecting mechanism 115 is disposed in the second compartment 122. The inlet 116 inlets a transport fluid to the resected grouting agent or osseus tissue. The outlet 117 outlets the transport fluid to a suctioning device 26. A portion of the outlet 117 is disposed in the second compartment 122. The visualizing device 113, the illuminating device 114, the first resecting mechanism 115, the inlet 116, and the outlet 117, all function is an integrated and coordinated manner. The visualizing device 113 includes a hollow metal sheath 123 and an eyepiece 124. A portion of the hollow metal sheath 123 is disposed in the first compartment 121. The eyepiece 124 is mechanically and optically coupled to the hollow metal sheath 123 at its proximal end 125. The eyepiece 124 is disposed at an angle and adjacent to the resecting mechanism 115. The visualizing device 113 includes a lens train 127 and a focusing lens 128. The lens train 127 has a plurality of lenses and is mechanically and optically coupled to the eyepiece 124 and disposed in the hollow metal sheath 123. The focusing lens 128 is mechanically and optically coupled to the lens train 127 and disposed in the hollow metal sheath 123 at its distal end 126. In an alternative embodiment the visualizing device 113 may include a coherent optical fiber and a focusing lens. The coherent optical fiber is mechanically and optically coupled to the eyepiece 124 and disposed in the metal sheath 123. The focusing lens 128 is mechanically and optically coupled to the coherent optical fiber and disposed in the metal sheath 123 at its distal end 126. A small video camera may be attached to the eyepiece 124. The illuminating mechanimsm 114 includes an optical fiber 129 and a light generator 21. A portion of the optical fiber 129 is disposed within the metal sheath 123 parallel to the lens train and is optically aligned with the lens train 127. U.S. Pat. No. 4,601,284, entitled Endoscope Connecting System, issued to Satoshi Arakawa and David H. Cooper on July 22, 1986, teaches a video camera which is optically coupled to an eyepiece, an optical-fiber connector which is disposed orthogonally to the eyepiece and a optical fiber. This is the standard arrangement of the prior art because the optical fiber needed to be out of the way of the surgeon's eye during endoscopy. Most endoscopy is now performed with a video monitor. In the present invention the eyepiece 124 and optical fiber 129 are disposed contiguously and parallel to one another so that a single cable bundle to the console 20 may be used. The light generator 21 generates light and is mechanically and optically coupled to the optical fiber 129. The illuminating device 114 provides illumination of the grouting agent or osseus tissue. A portion of the illuminating device 114 is disposed in the first compartment 121. The visualizing device 113, the illuminating device 114, the first resecting mechanism 115, the irrigating apparatus 116 and the aspirating apparatus 117 all function in an integrated and coordinated manner.

Figure 5:
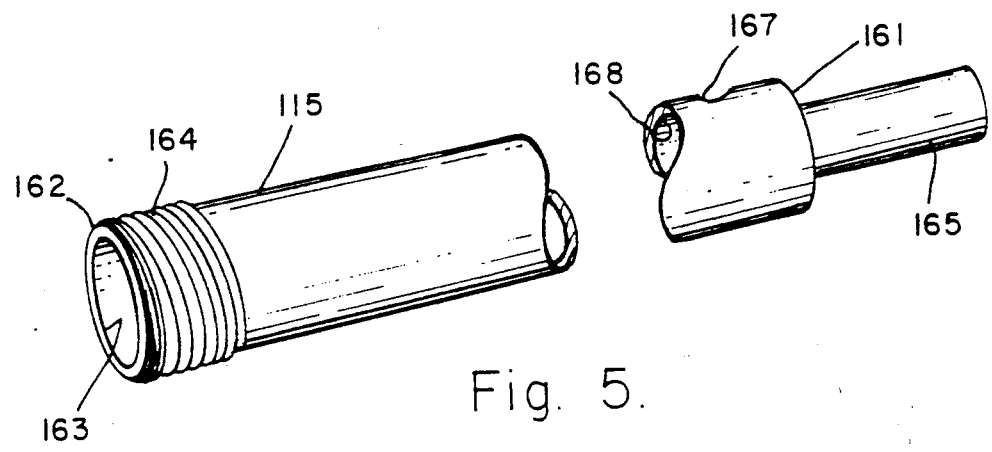
FIG. 5 is a partial perspective drawing of the first resecting mechanism of the first endoscopic viewing and resecting apparatus of FIG. 1.
Figure 6:
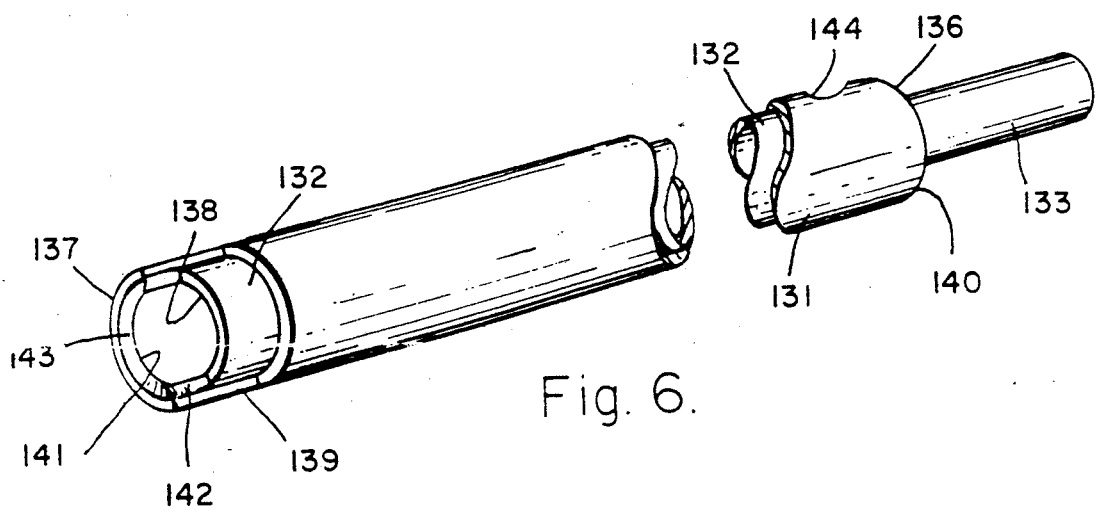
FIG. 6 is a longitudinal view in cross-section of second resecting mechanism of a second endoscopic resecting system which includes a console and an endoscopic viewing and resecting apparatus and which has been made in accordance with the principles of the second embodiment of the present invention.

Referring to FIG. 2 in conjunction with FIG. 3, FIG. 5, and FIG. 6 the first resecting mechanism 115 may include a hollow tube 166 and a driving mechanism 165, or an outer tube 131, an inner tube 132, and driving mechanism 133. The hollow tube 166 has a proximal end 161 and a distal end 162 and is disposed in the second compartment 122. The hollow tube 166 has an open distal end 163 and cutting flutes 164 just proximal to the open distal end 163. The hollow tube 166 has a window 167 near its proximal end. The driving mechanism 165 rotatively drives the hollow tube 166 so that the cutting flutes 164 abrade the grouting agent or osseus tissue. The resected grouting agent or osseus tissue and the transport medium is then aspirated into the the hollow tube 166 at the open distal end 163 of the hollow tube 166 and then moves through the lumen 168 of the hollow tube 166 to the window 167 near the proximal end 161 of the hollow tube 166. The outer tube 131 has a proximal end 136 and a distal end 137 and is disposed in the second compartment 122. The outer tube 131 has a first slot 138 with a first peripheral edge 139 at its distal end 137. The inner tube 132 has a proximal end 140 and a distal end 141 and is disposed coaxially with and rotatively coupled to the outer tube 131. The inner tube 132 has a second slot 142 with a second peripheral edge 143 at its distal end 141 and a window 144 at its proximal end 140. The driving mechanism 133 rotatively drives the inner tube 132 so that the first 139 and second 143 peripheral edges articulate thereby resecting the grouting agent or osseus tissue. The resected grouting agent or osseus tissue and transport medium is then aspirated into the lumen 146 of the inner tube 132 at the second slot 142 near the distal end 141 of the inner tube 132. The grouting agent or osseus tissue moves through the lumen 146 of the inner tube 132 to the window 144 near the proximal end 140 of the inner tube 132. The driving mechanism 133 includes an electric motor 151 and a power cord 152 the distal end of which is connected to the motor module 22. The window 144 is disposed adjacent to the outlet connector 134.

Referring to FIG. 7 a second resecting mechanism 214 includes a tube 215, an active electrode 216, a handpiece 217 and a generator 218. The tube 215 has a proximal end 219 and a distal end 220. A portion of the tube 215 is disposed in the second compartment 122 and has a window 221 at its proximal end 219. The outer surface 222 of the active electrode 216 is coated with a layer 223 of insulating material. A portion of the active electrode 216 is disposed within the tube 215. The active electrode 216 may be either monopolar or bipolar. The generator 218 generates electromagnetic energy in the radio frequency spectrum and is electrically coupled to the active electrode 216 so that the active electrode 216 is heated in order to resect the grouting agent or osseus tissue. U.S. Pat. No. 4,719,914, entitled Electrosurgical Instrument, issued to Gerald W. Johnson on Jan. 19, 1988, teaches an electrosurgical instrument. Each of U.S. Pat. No. 4,562,838, U.S. Pat. No. 3,974,833, U.S. Pat. No. 3,906,955, U.S. Pat. No. 2,888,928 teaches an electrosurgical instrument which has a tube and an electrode for use in high frequency electrocoagulation. The tube either supplies a liquid to the surgical site or aspirates blood and fluid, liquid and/or smoke from the surgical site.

Referring to FIG. 8 a third resecting mechanism 314 includes a tube 315, a transducer 316 and a generator 317. The tube 315 has a proximal end 318 and a distal end 319 and which is disposed in the second compartment 122. The tube 315 has a window 320 at its proximal end 318. The transducer 316 is mechanically coupled to the tube 314 and disposed at its proximal end 318. The generator 317 generates ultrasonic energy and is electrically coupled to the transducer 316 so that the transducer 316 causes the tube 315 to resonate in order to resect the target tissue. U.S. Pat. No. 4,750,902, entitled Endoscopic Ultrasonic Aspirators, issued to David G. Wuchinich, Robert Brendolan, Louis Katz, Donald R. Krawitt on June 14, 1988, teaches an endoscopic ultrasonic aspirator for removal of compliant biological tissues which includes irrigation and aspiration apparatus, a tube and a piezoelectric ultrasonic transducer. U.S. Pat. No. 4,681,561, entitled Ultrasonic Decoupling Sleeve, issued to Larry L. Hood and Maurice M. Imonti on July 21, 1987, teaches a decoupling sleeve for inclusion in a fluid conduit of an ultrasonically-operated surgical instrument. U.S. Pat. No. 4,587,957, entitled Ultrasonic Surgical Device, issued to Yasuo Noguchi and Masaru Shibata on May 13, 1986, teaches an ultrasonic surgical device which includes an ultrasonic transducer and a horn through which an irrigation fluid and surgical debris flow from the surgical site.

Referring to FIG. 10 a fourth resecting mechanism 414 includes a tube 415, a laser 416, and a lightguide 417. The tube 415 has a proximal end 418 and a distal end 419 and is disposed in the second compartment 122. The tube 415 has a window 420 at its proximal end 418. The laser 416 generates light energy. The light guide 417 is disposed in the tube 415 and guides the light energy so that the conversion of light energy to heat resects the grouting agent or osseus tissue. U.S. Pat. No. 3,528,424, entitled Laser Surgical Knife Equipment, issued to Waldemar A. Ayres on Sept. 15, 1979, teaches a laser generator and a light guide in conjunction with an articulated arm. Although the laser generator of U.S. Pat. No. 3,528,424, is a carbon dioxide laser, other laser generators including, but not limited to, an excimer laser, a ruby laser, an argon laser, an erbium:YAG laser and a neodymium:YAG laser with an without a contact sapphire tip may be used.

Accordingly, the endoscopic resecting system 10 can be used to remove a grouting agent or osseus tissue from the human body femoral canal under direct visual control. All of the energy sources for illumination, grouting agent or osseus tissue removal, and transportation of debris are conveniently located in the same modularized console 20 so that these processes of the operation are controlled and coordinated. The components of the endoscopic resecting system 10 placed partially within the femoral canal are organized in order to minimize the outer diameter of the compartmentalized tube 24 while still coordinating all of these functions to efficiently and quickly complete the grouting agent or osseus tissue removal process.

Direct visual control of the grouting agent or osseus tissue removal process reduces the incidence of or entirely precludes femoral canal perforation and damage to the underlying cortical bone, which in turn reduces the overall surgical morbidity of the operation, revision hip surgery, in that the patient does then not require a significantly larger surgical incision and longer general anesthesis time to treat the femoral canal perforation. Design of the system places components out of the way of the operating surgeon so components do not interfer with other aspects of the surgical procedure.

Visual control of the grouting agent or osseus tissue removal process obviates the need to use expensive flouroscopic equipment, reduces operating room personnel exposure to x-rays and also obviates the need for operating room personnel to wear heavy lead aprons during the entire operation. The devices are easier to use which reduces operating time and general surgery time. The endoscopic resecting system is inexpensive in comparison to the equipment which it replaces, and is easier to set up and maintain which further reduces expense.

From the foregoing it can be seen that an endosopic resecting system 10 has been described. It should be noted that the sketches are not drawn to scale and that distance of and between the figures are not to be considered significant.

What is claimed is:

1. An endoscopic resecting system for Viewing and resecting a grouting agent or an osseus tissue from the human body femoral canal, said endoscopic resecting system comprising:
  a. a compartmentalized tube with a first compartment of a first set of dimensions, a second compartment of a second set of dimensions larger than said first set of dimensions, a barrier between the first compartment and the second compartment made from an energy absorbing material, and an external, smaller diameter tube;
  b. visualizing means for directly viewing the grouting agent or the osseus tissue, a portion of said visualizing means being disposed in said first compartment;
  c. illuminating means for providing illumination of the grouting agent or the osseus tissue, a portion of said illuminating means being disposed in said first compartment;
  d. resecting means for resecting the grouting agent or the osseus tissue, a portion of said resecting means being disposed in said second compartment;
  e. friction reducing means whereby friction between the inside of the second compartment and the resecting means is minimized;
  f. vibration reducing means whereby vibration, created when the resecting means rotates at high speed, does not affect the visualizing means;
  g. inletting means contained for inletting a transport fluid to said resected target tissue, a portion of said inletting means being disposed in said smaller diameter external tube;
  h. outletting means for outletting said transport fluid to the suction device, a portion of said outletting means being disposed in said second compartment; and
  i. a console which contains energy form generating devices used to perform the resection under direct visual control, whereby said visualizing means, said illuminating means, said resecting means, said inletting means and said outletting means all function in an integrated and coordinated manner.

2. An endoscopic resecting system for viewing and resecting a grouting agent and an osseus tissue from the human body femoral canal according to claim 1 wherein said visualizing means comprises;
  a. a hollow metal sheath which has a proximal end and a distal end and a portion of which is disposed in said first compartment;

b. an eyepiece which is mechanically and optically coupled to said hollow metal sheath at its said proximal end, said eyepiece being disposed adjacent to said resecting means;

c. a lens train which has a plurality of lenses and prisms and which is mechanically and optically coupled to said eyepiece and disposed in said hollow metal sheath; and d. a focusing lens which is mechanically and optically coupled to said lens train and disposed in said hollow metal sheath at its said distal end.

3. An endoscopic resecting system for viewing and resecting a grouting agent and a target tissue from the human body femoral canal according to claim 1 wherein said visualizing means comprises:

a. a hollow metal sheath which has a proximal end and a distal end and a portion of which is disposed in said first compartment;

b. an eyepiece which is mechanically and optically coupled to said hollow metal sheath at its said proximal end, said eyepiece being disposed adjacent to said resecting means;

c. a coherent optical fiber which is mechanically and optically coupled to said eyepiece and disposed in said hollow metal sheath; and d. a focusing lens which is mechanically and optically coupled to said coherent optical fiber and disposed in said hollow metal sheath at its said distal end.

4. An endoscopic resecting system for viewing and resecting a grouting agent or an osseus tissue from the human body femoral canal according to claim 1 wherein said resecting means comprises:

a. a hollow tube which has a proximal end and a distal end and which is disposed in said second compartment, said hollow tube having an open distal end, a series of cutting flutes just proximal to the distal end, and a window near its proximal end;

b. driving means for rotatively driving said hollow tube so that the cutting flutes near the distal end abrade the grouting agent or the osseus tissue.

5. An endoscopic resecting system for viewing and resecting a grouting agent or an osseus tissue from the human body femoral canal according to claim 1 wherein said resecting means comprises:

a. an outer tube which has a proximal end and a distal end and which is disposed in said second compartment, said outer tube having a first slot with a first peripheral edge at its said distal end;

b. an inner tube which has a proximal end and a distal end and which is disposed coaxially with and rotatively coupled to said outer hollow tube, said inner tube having a second slot with a second peripheral edge at its said distal end and a window at Its said proximal end; and c. driving means for rotatively driving said inner tube so that said first and second peripheral edges articulate thereby resecting the grouting agent or the target tissue.

6. An endosopic resecting system for viewing and resecting a grouting agent or an osseus tissue from the human body femoral canal according to claim 2 wherein said illuminating means comprises:

a. An optical fiber a portion of which is disposed within said hollow metal sheath, said optical fiber aligned with said lens train, and said optical fiber aligned parallel to said lens train at said eyepiece of the visualizing means;

b. an additional optical fiber which is not disposed within the visualizing means;

c. a light generating means for generating light which is mechanically and optically coupled to said optical fiber.

7. An endoscopic resecting system for viewing and resecting a grouting agent or osseus tissue from the human body femoral canal according to claim 3 wherein said illumination means comprises:

a. an optical fiber a portion of which is disposed within said hollow metal sheath, said optical fiber aligned with said coherent optical fiber, and said optical fiber aligned parallel to said coherent optical fiber at said eyepiece of the visualizing means;

b. an additional optical fiber which is not disposed within said visualizing means; and c. a light generating means for generating light which is mechanically and optically coupled to said optical fiber.

8. An endoscopic resecting system for viewing and resecting a grouting agent or osseus tissue from the human body femoral canal according to claim 1 wherein said resecting means comprises:

a. a tube which has a proximal end and a distal end, a portion of said tube being disposed in said second compartment and having a window at its said proximal end;

b. an active electrode which is coated with a layer of insulating material and a portion of which is disposed within said tube; and c. generating means for generating electromagnetic energy in the radio frequency spectrum, said generating means being electrically coupled to said active electrode so that said active electrode is heated in order to resect the grouting agent or ossues tissue.

9. An endoscopic resecting system for viewing and resecting a grouting agent or osseus tissue from the human body femoral canal according to claim 1 wherein said resecting means comprises:

a. a tube which has a proximal end and a distal end and which is disposed in said second compartment, said tube having a window at its said proximal end;

b. a transducer which is mechanically coupled to said tube and disposed at its said proximal end; and c. generating means for generating ultrasoncic energy in the radio frequency spectrum, said generating means being electrically coupled to said transducer so that said transducer causes said tube to resonate in order to resect the grouting agent or osseus tissue.

10. An endoscopic resecting system for viewing and resecting a grouting agent or osseus tissue from the human body femoral canal according to claim 1 wherein said resecting means comprises:

a. a tube which has a proximal end and a distal end and which is disposed in said second compartment, said tube having a window at its said proximal end;

b. a laser which generates light energy;

c. a light guide which is disposed in said tube and is optically coupled to said laser so that conversion of said light energy to heat resects the target tissue.

11. A coordinated irrigating and aspsirating system comprising:

a. irrigating means for inletting a transport fluid to a resected grouting agent or osseus tissue;

b. aspirating for aspirating said transport fluid along with said resected grouting agent or osseus tissue to a suctioning apparatus;
c. outflow controlling means for controlling volume of inflow, said inflow controlling means being coupled to said irrigating means; and
d. outflow controlling means for controlling volume of outflow, said outflow controlling means being coupled to said aspirating means.

12. A coordinated visualizing and illuminating system comprising:
a. visualizing means for viewing tissue, said visualizing means including an eyepiece; and
b. illuminating means for illuminating said tissue, said illuminating means including an optical fiber which is disposed substantially parallel and adjacent to said eyepiece and a light generating means which is optically coupled to said optical fiber.

* * * * *